United States Patent
Masaro et al.

(10) Patent No.: US 7,754,229 B2
(45) Date of Patent: Jul. 13, 2010

(54) METHOD FOR PREPARING GELS

(76) Inventors: Laurent Masaro, 6100 Deacon, apt. 5N, Montréal, Québec (CA) H3S 2V6; Patrick Lapointe, 671 boul Talbot, Chicoutimi, Québec (CA) G7H 4A8; Jean-Charles Jacques Gayet, 5180 Walkley, apt 5, Montréal, Québec (CA) H4V 2M5

(*) Notice: Subject to any disclaimer, the term of this patent is extended or adjusted under 35 U.S.C. 154(b) by 1465 days.

(21) Appl. No.: 10/494,526

(22) PCT Filed: Nov. 14, 2002

(86) PCT No.: PCT/CA02/01745

§ 371 (c)(1),
(2), (4) Date: Dec. 21, 2004

(87) PCT Pub. No.: WO03/042300

PCT Pub. Date: May 22, 2003

(65) Prior Publication Data

US 2005/0106254 A1 May 19, 2005

Related U.S. Application Data

(60) Provisional application No. 60/331,414, filed on Nov. 15, 2001.

(51) Int. Cl.
*A61K 9/14* (2006.01)
*A61K 9/00* (2006.01)
(52) U.S. Cl. .................. 424/400; 424/486; 514/944
(58) Field of Classification Search .............. 424/400, 424/486; 514/944
See application file for complete search history.

(56) References Cited

U.S. PATENT DOCUMENTS

| 4,562,245 | A | | 12/1985 | Stageman |
| 5,225,227 | A | | 7/1993 | Yalpani |
| 5,229,158 | A | | 7/1993 | Yalpani |
| 5,962,626 | A | * | 10/1999 | Strande et al. ............ 528/295.5 |

(Continued)

FOREIGN PATENT DOCUMENTS

JP          11322962         5/1998

(Continued)

OTHER PUBLICATIONS

Doyle C. et al., 1991, Biomaterials, vol. 12, pp. 841-847.

(Continued)

*Primary Examiner*—Johann R Richter
*Assistant Examiner*—Abigail Fisher
(74) *Attorney, Agent, or Firm*—Ogilvy Renault, LLP

(57) ABSTRACT

The formation of a cream and gel is described using a biopolymer, such as a polyhydroxyalkanoate (PHA), a polylactide (PLA), a polylactideglycolide (PLGA) and a polyglycoside (PGA), or a derivative thereof, in a latex form with the addition of a binder, which is generally an amphiphilic chemical entity. An hydrophobic domain of the amphiphilic chemical entity interacts with at least one biopolymer forming a water soluble complex, while the hydrophilic domain of the amphiphilic chemical entity maintains the soluble complex in suspension in an aqueous solution, which after proper heating becomes a gel or a cream. As a result, a versatile gel or cream is created with different compositions and textures that are obtained based on the nature of the binder used and the ratio of biopolymers and binder(s).

12 Claims, 1 Drawing Sheet

U.S. PATENT DOCUMENTS

| | | | |
|---|---|---|---|
| 6,117,949 A * | 9/2000 | Rathi et al. | 424/426 |
| 6,146,665 A | 11/2000 | Marchessault et al. | |
| 6,193,991 B1 | 2/2001 | Shukla | |

FOREIGN PATENT DOCUMENTS

| | | |
|---|---|---|
| WO | WO 95/05153 | 2/1995 |
| WO | WO 97/05185 | 2/1997 |
| WO | WO 97/07229 | 2/1997 |
| WO | WO 97/21762 | 6/1997 |
| WO | WO 98/46782 | 10/1998 |
| WO | WO 98/46783 | 10/1998 |
| WO | WO 99/64498 | 12/1999 |
| WO | WO 01/35929 | 5/2001 |
| WO | WO 01/45742 | 6/2001 |

OTHER PUBLICATIONS

Fabri D. et al., 1998, Thermochimica Acta, vol. 321, pp. 3-16.
Galego N. et al., 2000, Polymer Testing, vol. 19, pp. 485-492.
Gangrade N. and Price J. C., 1991, Journal of Microencapsulation, vol. 8, No. 2, pp. 185-202.
Juni K. et al., 1986, Journal of Controlled Release, vol. 4, pp. 25-32.
Knowles J. C. et al., 1992, Biomaterials, vol. 13, No. 8, pp. 491-496.
Pouton C. W. and Akhtar S., 1996, Advanced Drug Delivery Reviews, vol. 18, pp. 133-162.
Turchetto A. and Cesàro A., 1995, Thermochimica Acta, vol. 269/270, pp. 307-317.
Williams S. F. et al., 1999, International Journal of Biological Macromolecules, vol. 25, pp. 111-121.

* cited by examiner

METHOD FOR PREPARING GELS

TECHNICAL FIELD

The present invention describes the use of biopolymers, and method for the production of gels or creams that can be used in cosmetic, cosmeceutical, pharmaceutical and food applications. In order to obtain a gel or a cream, the biopolymers are combined with amphiphilic chemical entities.

BACKGROUND OF THE INVENTION

Polyhydroxyalkanoates (PHAs) are natural polyesters produced by a large variety of microorganisms such as bacteria and algae. They are biodegradable thermoplastics obtained from renewable sources that can be processed with conventional equipment, which makes them very attractive for the plastic industry. The potential worldwide market for biodegradable polymers is enormous due to the extreme variety of applications. For example, degradable polymers can be used as films, sheets, fibers, foams, molded articles and many other products.

PHAs produced by microorganisms are intracellular granules accumulated as energy storage resulting of adverse growth conditions, i.e., nutrient limitation. The biopolymer accumulation in bacteria increases when a deficiency in nitrogen occurs. This deficiency is generally expressed by an increase of the ratio C/N, where C is the source of carbon and N the source of nitrogen actually in the culture medium. Therefore, the feeding strategy becomes a critical step that will have a direct impact on the productivity of the biopolymer. The food source is also an important factor that will decide the nature of the produced biopolymer. In fact, different homo- or copolymers can be obtained by varying the food source provided to the microorganism during the fermentation. The most well-known representatives of the PHA family are poly(3-hydroxybutyrate) (PHB) as well as its copolymer poly(3-hydroxybutyrate-co-3-hydroxyvalerate) (PHBV).

PHAs are biopolymers that are characterized by other numerous interesting properties. Among them, they are biocompatible and bioresorbable, which makes PHAs potent candidates for food, cosmetic and biomedical applications. An increasing number of publications and patents over the last years provide the best illustration. Yalpani reported the use of poly(hydroxy alkanoates) as fat substitute for food in the U.S. Pat. No. 5,229,158. Marchessault et al. described the use of PHA for the entrapment or microencapsulation of hydrophilic or lipophilic drugs in the U.S. Pat. No. 6,146,665. In this case, PHA is synthesized in vitro by polymerization of a hydroxyalkanoate coenzyme A monomer. Other controlled applications were published on PHA from bacterial sources.

The potential of PHA in drug delivery systems is now known in the art. PHAs are also used as implants in orthopedic surgery because of their biodegradability and bioresorption. For this particular use, PHAs are often reinforced with hydroxyapatite (Biomaterials, 1991, 12:841-847; Biomaterials, 1992, 13:491-496; Polymer Testing, 2000, 19:485-492). Numerous other implant applications were developed such as heart valves, vascular grafts and tissue engineering. Cosmetic composition containing hydroxy alkanoate derivatives was reported by Browser et al. in the International Patent Pub No. WO 95/05153. In this patent application, oligomers (1 to 5 monomer domains) of 2-hydroxyalkanoate derivatives are incorporated in the composition.

The solubility of these biopolymers is very low. They are totally insoluble in water and in most common organic solvents, which appear to be poor-solvents, with the exception of some halogenated solvents such as chloroform, dichloromethane and 1,2-dichloroethane. Traditionally, PHB is extracted by adding a PHA non-solvent to an halogenated solution containing the biopolymer (U.S. Pat. No. 4,562,245), which is not cost efficient as far as a large scale production is concerned. Therefore, the major concern about the extraction and purification of the biopolymer from the microorganism was the production cost. As a result, a lot of efforts were put forth to resolve this problem and many patents were issued. For example, method using PHA-poor solvent at high temperature (International Patent Pub. No. WO 98/46783), using non-halogenated solvents (International Patent Pub. No. WO 98/46782) and using marginal non-solvents (International Patent Pub. No. WO 97/07229). An aspect of the use of organic solvents at high temperature was the discovery of PHA gels once the solutions were allowed to cool at room temperature. Other examples of the formation of physical gel were found in the literature, Fabri et al. studied dilute solution of PHB in N,N-dimethylformamide and N-methyl-2-pyrrolidone (Thermochimica Acta, 1998, 321:3-16) whereas Turchetto and Cesbro used dimethylformamide (Thermochemica Acta, 1995, 269/270:307-317). The lower degree of solubility of polymers like PHAs in organic solvents was exploited by Dunn and English for drug release applications (International Patent Pub. No. WO 01/35929). These authors used a floating component containing the polymer and a bioactive agent that is administered to human by syringe and needle. Once introduced in the body, the solvent is dispersed and the polymer which is non soluble in water forms a solid matrix where the bioactive agent is trapped and further release.

One aspect of the purification and extraction process is the use of a dispersing agent of PHA in water by the addition of a surfactant (Patent Pub. No. WO 97/21762), but it does not lead to the formation of a gel neither of a cream.

U.S. Pat. No. 5,229,158 describes the use of PHA in a latex solution, with particle sizes that can get from 0.1 to 10 microns, which is similar to our statements. However, the main aggregating agents are totally different, for example pectin, lecithin and xanthan gum. No indication is given regarding the physical aspect of the final product neither its stability in time. PHA is used to substitute fat entities because it has a fat-like texture.

Moreover, the above-described applications and inventions have a limited range of concentration of PHA when organic solvents are used. In fact, it is impossible to obtain over a 5%. PHA solution (weight/volume) in organic solvents.

The stabilization of PHA dispersion in water as been reported in International Patent Pub. No. WO 97/21762. This application describes the use of amphiphilic chemical entities that would improve the solubility of the PHA in water and simplify the process of dispersion in order to purify the biopolymer during the extraction/purification processes. Dispersants used are for example dioctyl sulphosuccinate, sodium dodecylsulphonate, sodium dodecylbenzenesulphonate, sodium lauryl sarcosinate or sodium dodecyldiphenyl oxide disulphonate.

Different biodegradable copolymers have been described until now, including aliphatic polyester, polyorthoester, polyanhydride, poly alpha-amino acid, polyphosphagen, and polyalkylcyanoacrylate. Among aliphatic polyesters, polylactide (PLA), polyglycolide (PGA) and polylactideglycolide (PLGA) were approved as copolymers nontoxic to humans by the FDA. These copolymers were employed as drug delivery devices to carry the drugs or biomedical devices.

Based on the above-listed patents and publications which are quite representative of the state of the art relating to biopolymers, there is still considerable amount of work to do in order to improve the process of producing gels and creams because of the lack for methods to obtain a gel and/or a cream using biopolymers, particularly PHAs, that would be suitable principally for cosmetic and pharmaceutical applications. Such a process would rather use biocompatible and bioresorbing species.

It would be very much desirable to be provided with a new method for producing new biocompatible gels and creams composed with biopolymers.

SUMMARY OF THE INVENTION

One object of the present invention is to provide a method for producing or modulating a physical characteristic of aqueous gel composition comprising a biopolymer linked to a binder agent, the method comprising the steps of:

a) providing at least one biopolymer selected from the group consisting of polyhydroxyalkanoate (PHA), polycaprolactone (PCL), adipic acid, aminocoproic acid, poly(butylenes succinate), polylactide (PLA), polyglycoside (PGA), and polylactideglycolide (PLGA), or a derivative thereof, brought to the state of particles in suspension in an aqueous medium to form a latex;

b) combining the latex of step a) with at least one binder agent for a time and condition sufficient to form a soluble complex solution of biopolymer particles linked to the binder agent; and c) heating at between about 27° C. and 80° C. the soluble complex solution of step b), wherein at least one of the biopolymer of step a) or the binding agent of step b) are in determined concentration and the heating of step c) is long enough to obtain a desired physical characteristic of the gel composition.

The binder may be an amphiphilic molecules or a molecule comprising at least one hydrophilic domain such as, but not limited to, a polyethylene glycol (PEG), and at least one hydrophobic domain, such as for example a fatty acid, or a derivative thereof.

The gel composition of the invention may be a viscous liquid or a solid gel.

Another object of the present invention is to provide an aqueous gel composition comprised of at least one biopolymer selected from the group consisting of polyhydroxyalkanoate (PHA), polycaprolactone (PCL), adipic acid, aminocoproic acid, poly(butylenes succinate), polylactide (PLA), polylactideglycolide (PLGA) and polyglycoside (PGA), or a derivative or a mixture thereof, and at least one binder agent.

The binder may be an amphiphilic molecule or a molecule comprising at least one hydrophilic domain such as but not limited to, polyethylene glycol (PEG) and at least one hydrophobic domain, such as a fatty acid, or a derivative thereof.

For the purpose of the present invention, the following terms are defined below.

The term "amphiphilic" as used herein is intended to mean a chemical compound having a hydrophilic domain and at least one hydrophobic terminal domain.

The term "biopolymer" as used herein is intended to mean polymers obtained from natural and renewable sources and which mode of synthesis occurs naturally such as with plants or microorganisms.

The term "polymer" as used herein is intended to mean macromolecules synthesized by chemical reaction or obtained from petroleum sources, even if one of the components (monomer, precursor, etc.) is obtained from natural and renewable sources. PLA, PGA, PLGA, and PCL will be recognized as polymers to one skilled in the art.

The term "binder" as used herein is intended to mean amphiphilic chemical compound capable to associate with PHA granules, which are hydrophilic, and remain soluble in aqueous phase simultaneously. For example, but not limited to, a binder can be constituted of two hydrophobic domains separated by a hydrophilic domain.

The term "cream" as used herein is intended to mean a solution with enhanced viscosity properties which does not imply necessarily the formation of a three-dimensional network due to polymer chain entanglement.

The term "gel" as used herein is intended to mean a three-dimensional network organization swelling in a solvent. When water is the solvent, the gel may be defined as "hydrogel". Further, the three-dimensional network is due to polymer chain entanglements for a physical gel, whereas it is due to chemical bonds for a chemical gel.

The terms "granule" and "particle" as used herein are intended to mean spheroids shaped biopolymer segments with particle size distribution from 0.1 to 10 μm, preferably form 0.2 to 5 μm.

The term "latex" as used herein is intended to mean a suspension of PHA granules and/or particles. A latex as defined herein may comprise an aqueous medium as diluent or solvent. The PHA granules can be either in their native state or re-suspended in water. The native PHA is defined as a granule of PHA, produced by bacterial fermentation, which was never precipitated, therefore its crystallization degree remains close to or slightly higher than what it was in the bacteria, i.e., very weak. The latex may have the aspect of milk in color and texture, while the viscosity may be similar to that of water.

The term "hardness" as used herein is intended to mean the force required to obtain a deformation of a body. The hardness measurement units are most of the time expressed in Newton. A Newton is a unit of force equal to the force that produces an acceleration of one meter per squared second of a mass of one kilogram.

The term "cohesiveness" as used herein is intended to mean the strength of the internal bonds making up the body of the cream or gel. It can be defined as the molecular force between particles within a body or substance that acts to unite them.

The term "viscosity" as used herein is intended to mean the rate of flow per unit of force (milli Pascal-seconds (mPa·s) or centiPoises (cPs)). The viscosity is the property of a fluid that resists the force tending to cause the fluid to flow. mPas is a milliPascal second. A pascal is the unit of pressure or stress, equal to one Newton per square meter.

Consistency can be defined as a quality of a gel or a cream which is perceptible to touch. The term 'body' can also be used to express consistency. A broader definition can be used when referring to consistency as a characteristic of a mixture of cream and gel substances, or as the touch feel characteristics of semi-solids or liquids. Hence, sensory concepts such as touch feel and body could be associated with consistency. Consistency could be empirically evaluated with apparatus such as the Adams consistometer or the Bostwick consistometer. The measure of consistency is usually presented as centimeters per 30 seconds when the Bostwick consistometer is used.

The term "elasticity" as used herein is intended to mean the rate at which deformed gels or creams go back to their original undeformed state after removal of the force. The measurement unit of elasticity is expressed in millimeters or in percentage. The elasticity is the property of a substance that enables it to change its length, volume, or shape in direct response to a force effecting such a change and to recover its original form upon the removal of the force.

The term "adhesion" as used herein is intended to mean the force necessary to overcome the attractive forces between the surface of a matter and the surface of an other material with which it is in contact. The adhesion is the attractive molecular force that tends to hold together unlike bodies where they are in contact. The measurement unit of the adhesion is expressed in Newton.

DETAILED DESCRIPTION OF THE PREFERRED EMBODIMENT

Figure 1:
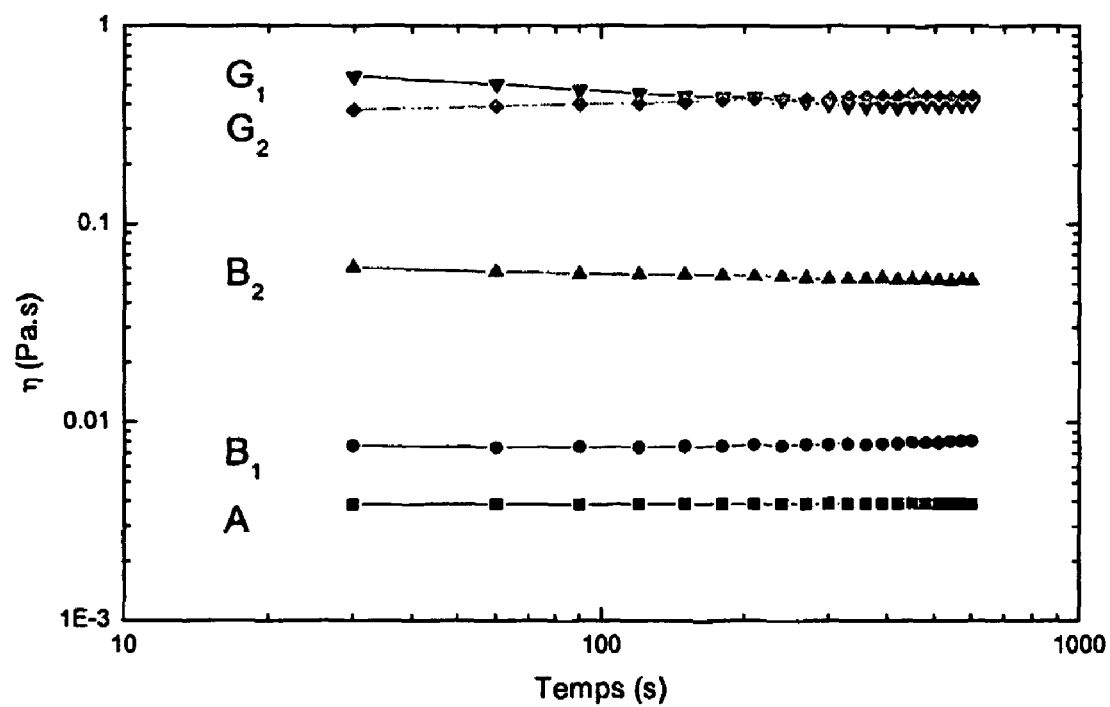
FIG. 1 illustrates the evolution of the viscosity (Pa·s) versus the time (s) for a fixed strain and temperature for gel and cream solutions.

In accordance with the present invention, a method of producing biocompatible gels and creams based on linking biopolymers, such as polyhydroxyalkanoate (PHA), polylactide (PLA), polyglycoside (PGA), polylactideglycolide (PLGA), and polycaprolactone (PCL) with a binder agent, preferably an amphiphilic chemical entity, in a aqueous medium in order to obtain a gel or a cream is provided.

The Applicant has discovered that by combining certain types of biopolymer to specific binding agents, such as amphiphilic agents, the resulting suspension may, depending of the processing conditions to prepare the mixture of these products, allows the aqueous dissolution of the biopolymer and induces the formation of gels or creams having different levels of density, firmness, and/or viscosity.

In one embodiment of the present invention, at least one binder is added to a biopolymer latex solution. The resulting product is a cream or a gel having improved or enhanced viscosity when compared to the viscosity of the latex or the binder itself in water, as well as an increase in the time of sedimentation of the PHA granules, which is almost infinite because the resulting product is extremely stable in time and temperature.

Applications where plastic products have a single use and/or short life are ideally suited in the case of PHAs, because at once used these products are entirely converted in compost sites or can be metabolized in biological conditions.

According to another embodiment of the present invention, the gels or creams issued from the method of the invention may comprise only one biopolymer or a mixture of different biopolymers configured into mono- or or multiblocks copolymers. These copolymers may be combinations of, polypropylene oxide, PHA, PLA, PLGA and PCL.

The invention is applicable to create a cream and/or a gel from any type of PHA biopolymer produced by plants or microbial organisms either naturally or through genetic engineering, as well as PHA polymers chemically synthesized.

According to one other embodiment of the invention, the PHA biopolymers used are polyesters composed of monomer units having the formula:

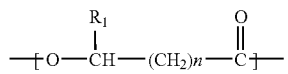

wherein n is an integer from 1 up to 9; $R_1$ is preferably an H, alkyl or alkenyl. Alkyl and alkenyl side chains are preferably from $C_1$ up to $C_{20}$ carbon long. PHA biopolymers can be homopolymers, with the same repeating monomer unit, and/or copolymers, with at least two different repeating monomer units.

Copolymers can be structured statistically, random-block, alternating or grafted. Molecular weights of the PHA biopolymers are generally in the range of 1,000 to 2,000,000 g/mol, preferably between 10,000 and 1,500,000 g/mol, and more preferably between 5,000 and 1,000,000 g/mol. The orientation of the monomers can be, for example, head to head, head to tail or tail to tail.

PHAs that can be used according to this invention may include poly(3-hydroxybutyrate), poly(3-hydroxyoctanoate), poly(4-hydroxybutyrate), poly(3-hydroxybutyrate-co-3-hydroxyvalerate), poly(3-hydroxybutyrate-co4-hydroxybutyrate) and poly(3-hydroxybutyrate-co-3-hydroxyoctanoate).

Copolymers of PHA, listed herein above, may be in the range of 40 to 100% of monomer 3-hydroxybutyrate and preferably between 60% and 95%.

According to this invention, the PHA concentration in the latex solution is from 0.01% to 50% and including, preferably from 1% to 45% and more preferably from 5% to 40%. Concentrations are expressed weight/volume. The latex can be obtained from a native biopolymer or dissolved from a dry powder. In the latter case, the high crystallinity of the biopolymer can affect the texture of the final cream and/or gel. This problem can be overcome by producing amorphous polymer suspension as described in International Patent Publication WO 99/64498 incorporated herein by reference.

According to the invention in its first aspect, the addition of a binder to biopolymer latex solutions is characterized by its transformation into a cream and/or a gel, which results in an increase in the viscosity or firmness and a better solution stability. Both phenomenon may be associated to the amphiphilic characteristic of the binder which contains a plurality of domains—at least 2 and to several 10, and typically 3 with opposite properties: hydrophilic and hydrophobic.

One structure of the binder may be a tri-block chemical compound, having two hydrophobic end domains and one core hydrophilic domain. It is assumed that the hydrophobic end domain is more easily associated with the hydrophobic PHA granules, for example, the hydrophilic core remains in the aqueous phase, thus creating a bridge between the granules and allowing interaction with water molecules. A physical gel is then obtained, i.e., reversible and with lower mechanical properties than a chemical gel. A similar phenomenon is assumed with two-domain amphiphilic compounds. The hydrophobic domain is associated with the biopolymer chains in suspension in water while the hydrophilic chains interact themselves in the aqueous phase. As a result, the cream or gel so obtained is less physically resistant to stress and strain.

Hydrophobic domain may be for example aliphatic chains $C_nH_{2n+2}$ ranging from $C_1$ to $C_{40}$, linear and/or branched out. Unsaturated alkyl chains ranging from $C_2$ to $C_{40}$, with one or more unsaturated bond, linear and/or branched chains including one or more aromatic moieties. In the case of a tri-block sample with hydrophobic domain at both ends, only one had to be long enough to associate with the PHA chain, the other can be shorter.

Hydrophobic domain may contain one or more heteroatoms (nitrogen, oxygen, sulfur, chlorine, fluorine, etc.), individually or mixed. For example, poly (propylene glycol) is an hydrophobic compound with an oxygen heteroatom in the main polymeric chain and an alkyl branched out, a methyl group.

Hydrophobic domain can be for example saturated fatty acids with an alkyl chain from $C_{10}$ to $C_{30}$, preferably between $C_{14}$ and $C_{24}$. For example, lauric, myristic, palmitic, stearic, arachidic, behenic, lignoceric acids. Hydrophobic domain can also be unsaturated fatty acids, having one or more insaturation, with alkyl chain from $C_{10}$ to $C_{30}$, preferably between $C_{14}$ and $C_{24}$. For example, palmitoleic, oleic, linoleic, α-linolenic, γ-linolenique, arachidonic, eicosapentaenoic, and nervonic acids. Binders can have one or two fatty acids at their ends, or derivatives thereof.

Molecular organization of the binder may be a two- or tri-block sample with one or two (similar or with groups from more than one chemical composition) hydrophobic domain mentioned above, respectively.

Hydrophilic domain may be for example non ionic chemical entities such as polyalkylene oxide, especially polyethyleneoxyde, glycoside, or polyglycerol or amine oxide. Hydrophilic domain may have ionic entities such as carboxylate, sulphate, sulphonate, phosphate, phosphanate or ammonium. Hydrophilic group of the binder may contain more than one chemical composition from the list above mentioned. The most suitable hydrophilic domain is the polyethylene glycol and derivatives of formula

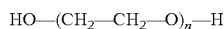

where n is an integer varying from 1 to 2,500, preferably between 7 and 500. Hydrophilic domain may also be an hydrophilic polymer which is miscible with PHA, such as poly(vinyl alcohol), poly(vinyl acetate), poly(epichlorohydrin), polybutylacrylate, poly(methyl methacrylate), poly (ethyl methacrylate) and polysaccharides.

The quantity as well as the nature of the binder necessary to obtain a gel is closely linked to the concentration of PHA in the latex solution. If the latter is very diluted, the binder should contain a large molecule, the equivalent of an oligomer for example, and its concentration should be important. Moreover, the distribution between the hydrophobic and hydrophilic domains should allow a good interaction between the binder and the PHA granule. In other words, when the concentration in latex is low, the hydrophobic domain should be long enough to induce the interaction with the PHA granules. To the opposite, for higher latex concentration, the length of the hydrophobic domain does not need to be very long, but the length of the hydrophilic core domain needs to be long enough to maintain a cohesion with the aqueous medium. In brief, to form a gel with a dilute latex solution it is necessary to use a long binder with an elevated ratio of hydrophobic versus hydrophilic domains, while it is necessary to use a shorter binder with a lower ratio hydrophobic versus hydrophilic domains for a concentrated latex solution.

In one embodiment of the present invention, a short binder with a low ratio hydrophobic versus hydrophilic domains may be used with a thin latex solution to give a cream. The same result may be obtained when a concentrated latex solution is used with a long binder having an elevated ratio of hydrophobic versus hydrophilic domains.

According to the present invention, the concentration of the binder (added to the latex solution) in the final formulation is between 0.01% and 75%, preferably between 1% and 30% and rather between 2% and 20%. Concentrations are expressed weight/volume. The binder can be used alone or mixed at least 2 to several 10 or so with the either the same concentration or not. The nature of the binders added can also vary. For example, a binder with a short length and another with a long one. The ratio of the hydrophobic domains versus the hydrophilic domain can be similar or different, in the case of tri-block binders. One or several di-block binders can be added with one or several tri-block binders.

According to the present invention, another embodiment is the use of these creams and gels described above, for the delivery of chemical compounds and/or cells in food, cosmetic, cosmeceutical and pharmaceutical applications for humans as well as animals. In fact, all the components, the biopolymer as well as the binder agent, used in the preparation of the gels and creams are biocompatible and bioresorbing.

In one embodiment of the present invention, one step of the method invention comprises the modulation of at least one parameter of a gel or cream Theological profile in manner to allow the gel or cream composition at use to have a desired hardness, elasticity, cohesion, gumminess, consistency, viscosity and yield stress.

According to another embodiment of the invention, there is provided a method in which a quantitative and descriptive approach is used to adapted the gel or cream texture in, for example, alimentary, cosmetical, cosmeceutical or pharmaceutical applications. A description of textural characteristics of creams and gels is provided and prones to be an integral part of the alimentary, cosmetical, cosmeceutical or pharmaceutical applications. No publication has reported quantified gel or cream texture in relation to its importance in the health care of alimentary, cosmetical, cosmeceutical or pharmaceutical applications. Rheology is now offering a promising avenue in a more objective and optimized applications.

Rheology is the study of the deformation and flow of gel and cream compositions. It offers vocabulary and specific terminology to discuss these compositions and their textural characteristics. Gels and creams vary greatly in composition and show a vast array of textural characteristics. Liquids could be viscous and thick like molasses or fluid and thin like water. Solids also vary in texture. Solids could be adhesive. Rheology also offers several instruments such as viscometers and texturometers which permit quantification of these textural characteristics.

Rheology of Liquids

Viscosity is the internal friction of a fluid or its resistance to flow. It is a textural parameter that could be evaluated by fundamental testing which quantifies the flow of fluids. Instrumental devises such as capillary flow, Couette or Searle flow, parallel-plate or cone-and-plate viscometers could be used to determine viscosity. Isaac Newton was the first to express the law of ideal liquids can be described the flow behavior of ideal liquids as $$\eta = \sigma/\gamma \qquad \text{(Equation 1)}$$

where η is the viscosity (Pa·s), σ is the shear stress (Pa) and, γ is the shear rate ($s^{-1}$).

Ever since, fluids are mainly classified as Newtonian or non-Newtonian. A linear relationship of the shear stress (σ) expressed in Pascal as a function of shear rate (γ) expressed in $s^{-1}$ illustrates the flow behavior of ideal liquids. A Newtonian liquid will have a constant slope that will express viscosity (η). The Newtonian liquids present flow characteristics that are influenced only by temperature and gel or cream compositions. The Newtonian gel or cream compositions are not affected by shear rate and shear history.

Non-Newtonian liquids are affected by temperature, gel or cream compositions and shear rate. The apparent viscosity ($\eta_a$) is then used to express the viscosity and is specific to the shear rate at which the product is tested. Non-Newtonian gel or cream compositions could further be divided as time-independent or time-dependent. The latter, contrary to time-independent fluids, will show an apparent viscosity that will be affected by the length of time for which the shear is applied. Time-independent fluids could be either pseudoplastic (i.e. shear-thinning, losing viscosity with time at a varying shear rate) or dilatant (i.e. shear-thickening, gaining viscosity over time) which is rarely encountered. Shear-thinning could be explained by re-orientation, stretching, deformation or disaggregation of molecules, which compose the tested product, following shear. Therefore, important decrease in viscosity could be observed in products after the shearing.

Time-dependent flow characteristics are further divided into thixotropic and rheopectic liquids. The former displays a decrease in viscosity when a constant shear rate is applied for a certain period of time.

The latter presents an increase in viscosity over time when the shear rate is maintained constant.

One particular embodiment of the present invention is a method allowing the modulation of at least one of the physical characteristics described herein, as the viscosity, the consistency, the firmness or hardness, the yield stress, the elasticity, the cohesiveness, or the adhesion of a gel and/or a cream. For example, but without limiting it to, the consistency may have a value of between about 1 to 50 cm per 30 seconds, the viscosity between about 50 to 10 000 mPa, the yield stress between about 1 to 500, the elasticity between about 1 to 90%, the hardness between about 0,1 to 100 Newton, the cohesiveness between about 0.01 to 25, and the adhesion between about 0.01 to 100 Newton.

In performing the method of the present invention, one or more of the physical characteristics can be adjusted or modulated through different combination of biopolymers and binding agents.

The present invention will be more easily understood by referring to the following examples which are given to illustrate the invention rather than to limit its scope.

EXAMPLE I

Production of PHA Cream with PEG 900

The concentration of PHA in the latex obtained after fermentation, extraction and purification is 20% w/v. The binder used in this example is poly(ethylene glycol) distearate, PEG-distearate, of molecular weight 930 g/mol, which implies that the poly(ethylene glycol) part corresponds to 9 ethylene glycol repeating monomer units.

0.8 gram of PEG-distearate is added to 20 mL of latex solution, and heated to 40° C. for 1 hour under moderated stirring and sealed to prevent water evaporation. The solution obtained is homogeneous and more viscous than the initial latex solution. Moreover, when PEG-distearate is dissolved in water to obtain a similar solution, 4% w/v, its viscosity is lower than the gel described above.

The cream remains stable in viscosity and does not settle down with variation in time and temperature. After 4 weeks, the gel still remains stable when kept sealed at room temperature. A similar result is observed with a sample kept sealed in a refrigerator at 4° C.

EXAMPLE II

Production of PHA Cream with PEG 6000

In this example, a similar product is developed with a PEG-distearate having a PEG part with a molecular weight of around 6,000 g/mol instead of 396 g/mol, which represents between 130 and 140 ethylene glycol repeating monomer units. The hydrophobic end parts of the binder in this example do not change, only the central hydrophilic part.

0.8 gram of PEG-distearate is added to 20 mL of latex solution, and heated to 40° C. for 1 hour under moderated stirring and sealed to prevent water evaporation. The solution obtained is homogeneous and more viscous than the initial latex solution or the same PEG-distearate solution in water. However, this solution is less viscous than the previous solution obtained with a shorter PEG domain. The stability in time and temperature is not affected and is similar to the previous one.

EXAMPLE III

PHA Latex and Mono Fatty Acid-co-PEG

In this example, a cream is developed with a PEG having a single fatty acid. The hydrophobic end part of the binder is an oleic acid, i.e., insaturated fatty acid with the same length as stearic acid. The hydrophilic part is also slightly shorter than in the first example, total molecular weight of PEG is 860, which gives about 5 repeating ethylene glycol monomer units.

3.57 mL of PEG-monooleate is added to 20 mL of latex solution, and heated to 40° C. for 1 hour under moderated stirring and sealed to prevent water evaporation. The PHA concentration in the latex is 30%. The solution obtained has a cream like structure, i.e., homogeneous and more viscous than the initial solutions. This cream remain relatively stable in time like the previous ones, but do not show the same extend of temperature stability. Further, it is less viscous than the ones described in the two first examples.

EXAMPLE IV

PHA Latex and PPO-PEO-PPO

In this example, a gel is made with a different triblock sample based on poly(propylene glycol) and PEG. Such samples are commonly called poloxamer.

4 mL of poloxamer P181 was added to a latex solution in order to obtain a 20 mL solution. The PHA concentration in the latex is 40%. After few minutes an gel like composition is obtained which is homogenous and stable. If the mixture is headed to 40° C., a more firm and consistent gel like composition is obtained. In addition, water is expelled from the gel, providing a clear and distinct phase.

EXAMPLE V

Rheological Measurements

Five solutions were tested using a rheometer AR 2000 (Advance Rheometer). Solution A is a latex of a copolymer (PHB-HV 95-5), with a specific concentration of 20% w/v. Solution $B_1$ and $B_2$ are made of poly(ethylene glycol) distearate of molecular weights 930 and 6000, respectively, with concentration of 4% w/v. Solutions $G_1$ and $G_2$ result of the mixture of a latex solution with solution $B_1$ or $B_2$ as previously described in Examples I and II.

All experiments were realized at 37° C. and constant shear stress of 1 Pa excepted for sample $B_1$ (10 Pa) because its consistency is much more harder than the other samples. As shown on FIG. 1, the viscosity of the gels ($G_1$ and $G_2$) are much more higher than the viscosity of each constituent (A+B$_1$ and A+B$_2$ respectively). The increase in viscosity for samples G$_1$ and G$_2$ is a clear evidence of the interaction between the constituents that it the core of the invention and was described in details previously.

While the invention has been described in connection with specific embodiments thereof, it will be understood that it is subject to further modifications and this application is intended to cover any variations, uses, or adaptations of the invention following, in general, the principles of the invention and including such departures from the present disclosure as come within known or customary practice within the art to which the invention pertains and as may be applied to the essential features set forth hereinbefore, and as follows in the scope of the appended claims.

What is claimed is:

1. A method for producing an aqueous gel composition comprising a biopolymer crosslinked to a binding agent, said method comprising the steps of:
    a) providing at least one biopolymer selected from the group consisting of polyhydroxyalkanoate (PHA), polylactide (PLA), polyglycoside (PGA), polylactideglycolide (PLGA), and polycaprolactone (PCL), in the form of particles in suspension in an aqueous medium forming a latex;
    b) contacting said latex of step a) with said binding agent wherein said binding agent is a molecule comprising at least one hydrophilic domain and a hydrophobic domain, for a time and conditions sufficient to form an soluble complex solution of biopolymer particles mixed with said binding agent; and
    c) heating said soluble complex solution of step b) at between 27° C. and 70° C. for a time sufficient to crosslink said biopolymer and binding agent to increase viscosity of said solution from step b) to form said gel;
    wherein said hydrophilic domain is polyethylene glycol, and said hydrophobic domain is a fatty acid.

2. The method of claim 1, wherein said aqueous gel composition is a viscous liquid or a solid gel.

3. An aqueous gel composition comprising at least one biopolymer selected from the group consisting of a polyhydroxyalkanoate (PHA), a polylactide (PLA), a polylactideglycolide (PLGA) and a polyglycoside (PGA), polycaprolactone (PCL), crosslinked with at least one binding agent, said binding agent being a molecule comprising at least one hydrophilic domain and a hydrophobic domain:
    wherein said hydrophilic domain is polyethylene glycol, and said hydrophobic domain is a fatty acid.

4. The aqueous gel of claim 3, wherein said aqueous gel composition is a viscous liquid or a solid gel.

5. A method for modulating viscosity of a composition comprising a biopolymer crosslinked to a binding agent, said method comprising the steps of:
    a) providing at least one biopolymer selected from the group consisting of polyhydroxyalkanoate (PHA), polylactide (PLA), polyglycoside (PGA), polylactideglycolide (PLGA), and polycaprolactone (PCL), in the form of particles in suspension in an aqueous medium forming a latex;
    b) contacting said latex of step a) with a binding agent said binding agent being a molecule comprising at least one hydrophilic domain and a hydrophobic domain, for a time and conditions sufficient to form a soluble complex solution of biopolymer particles mixed with said binding agent; and
    c) heating said complex solution of step b) at between 27° C. and 70° C. for a time sufficient to crosslink said biopolymer and binding agent to increase viscosity of said solution from step b) to form a gel;
    wherein said hydrophilic domain is polyethylene glycol, and said hydrophobic domain is a fatty acid.

6. The method of claim 5, wherein said aqueous gel composition is a viscous liquid or a solid gel.

7. The method according to claim 1, wherein said biopolymer is PHA.

8. The method of claim 7, wherein said binding agent is selected from the group consisting of PEG-distearate and PEG-monooleate.

9. The composition according to claim 3, wherein said biopolymer is PHA.

10. The composition of claim 9, wherein said binding agent is selected from the group consisting of PEG-distearate and PEG-monooleate.

11. The method according to claim 5, wherein said biopolymer is PHA.

12. The method of claim 11, wherein said binding agent is selected from the group consisting of PEG-distearate and PEG-monooleate.

* * * * *